United States Patent
Ammer et al.

(10) Patent No.: US 11,644,474 B2
(45) Date of Patent: May 9, 2023

(54) USE OF MACIMORELIN IN ASSESSING GROWTH HORMONE DEFICIENCY IN CHILDREN

(71) Applicant: Æterna Zentaris GmbH, Charleston, SC (US)

(72) Inventors: Nicola Ammer, Frankfurt (DE); Michael Teifel, Weiterstadt (DE); Beate Aue, Aschaffenburg (DE)

(73) Assignee: ÆTERNA ZENTARIS GMBH, Frankfurt am Main (DE)

( * ) Notice: Subject to any disclaimer, the term of this patent is extended or adjusted under 35 U.S.C. 154(b) by 0 days.

(21) Appl. No.: 17/375,709

(22) Filed: Jul. 14, 2021

(65) Prior Publication Data

US 2022/0026449 A1    Jan. 27, 2022

Related U.S. Application Data

(60) Provisional application No. 63/054,889, filed on Jul. 22, 2020.

(51) Int. Cl.
  *G01N 33/74* (2006.01)
  *A61K 38/27* (2006.01)
  *G01N 33/49* (2006.01)

(52) U.S. Cl.
  CPC ........... *G01N 33/74* (2013.01); *A61K 38/27* (2013.01); *G01N 33/49* (2013.01); *G01N 2333/61* (2013.01); *G01N 2800/04* (2013.01); *G01N 2800/38* (2013.01)

(58) Field of Classification Search
  CPC ............... A61K 38/27; G01N 2333/61; G01N 2800/04; G01N 2800/048; G01N 2800/38; G01N 2800/52; G01N 33/48; G01N 33/49; G01N 33/68; G01N 33/74
  USPC ........... 514/11.3, 11.4; 436/63, 86, 87
  See application file for complete search history.

(56) References Cited

U.S. PATENT DOCUMENTS

| | | | |
|---|---|---|---|
| 8,192,719 B2 * | 6/2012 | Larsen | G01N 33/74 702/9 |
| 9,763,919 B2 * | 9/2017 | Thorner | A61K 31/435 |
| 10,288,629 B1 * | 5/2019 | Ammer | G01N 33/5091 |
| 2010/0216706 A1 * | 8/2010 | Horvath | A61P 25/00 514/212.07 |

OTHER PUBLICATIONS

Garcia et al. Journal of Clinical Endocrinology & Metabolism, vol. 103, No. 8, pp. 3083-3093, May 31, 2018.*
Garcia et al. Journal of Clinical Endocrinology & Metabolism, published online Apr. 4, 2013 as doi:10.1210/jc.2013-1157, pp. 1-8.*
Agrawal et al. Expert Reviews of Molecular Diagnostics, vol. 14(6), pp. 647-654, Jun. 30, 2014.*
Csakvary et al. Hormone Research in Paediatrics, vol. 94, pp. 239-250, Aug. 26, 2021.*

\* cited by examiner

*Primary Examiner* — Maureen Wallenhorst
(74) *Attorney, Agent, or Firm* — Kilpatrick Townsend & Stockton LLP

(57) ABSTRACT

The present invention provides a method for measuring growth hormone level in a human child, including a method of assessing pituitary-related growth hormone deficiency in a human child as a stand-alone test. The method includes the steps of oral administration of an effective amount of macimorelin to the child, collecting from the child two or three post-administration blood samples within a range of about 60 minutes after administration, and determining the level of growth hormone in the samples. The method can be used for diagnosing pituitary-related growth hormone deficiency in a child when the peak level of determined growth hormone in the samples is below a cut-off value.

7 Claims, 3 Drawing Sheets

Cohort 1

Cohort 2

Cohort 3

Cohort 1

Cohort 2

Cohort 3

USE OF MACIMORELIN IN ASSESSING GROWTH HORMONE DEFICIENCY IN CHILDREN

This application claims priority to U.S. Provisional Patent Application No. 63/054,889, filed Jul. 22, 2020, the contents of which are hereby incorporated by reference in the entirety for all purposes.

BACKGROUND OF THE INVENTION

Growth Hormone Deficiency (GHD) is a disease which in children is characterized by a reduction in mycological parameters, like growth failure and short stature. GHD in children can be congenital or acquired and either isolated or combined with other pituitary hormone defects. There are many well-defined causes of GHD in children, but the cause is often unknown (idiopathic GHD). The definitions of the various types of GHD and other causes of short stature are given in the International Classification of Pediatric Endocrine Diagnoses (ICPED). If untreated, childhood-onset GHD leads to permanent short stature. In children, the diagnosis of GHD rests on a detailed medical history, clinical features, growth (auxological) analysis, biochemical tests of components of the GH-IGF axis and radiological assessment of skeletal maturation and of pituitary anatomy using MRI (GHRS, 2000).

Similar to the situation in adults, the diagnosis of GHD in children depends on various biochemical tests which are based on growth hormone stimulation tests (GHSTs) determining the growth hormone (GH) levels that can be induced with agents known to stimulate the release of GH. GHSTs currently in use, like the ITT or the glucagon stimulation test (GST), have not been developed and approved specifically for this purpose but were adapted from other indications, and thus have limitations with regard to performance characteristic (sensitivity of specificity), safety, or feasibility (Molitch et al., 2011; Cook et al., 2009).

Additionally, there is considerable controversy about the role of GH stimulation testing in pediatric patients, since low GH levels in provocation tests frequently occur and there are concerns about the validity and reproducibility of GHSTs.

Accordingly, guidelines for the diagnosis of GHD in children commonly require that not only one GHST is being conducted but that the outcome of two GHSTs is required to conclude on the diagnosis of GHD, unless there are typical brain defects which would require the use of one GHST only (GHRS, 2000, GHRS 2019; Guzzetti 2019).

The consensus guidelines of the GH Research Society published in 2000 (GHRS, 2000), as well as the American Association of Clinical Endocrinologists guidelines published in 2003 (Gharib, 2003) and national guidelines (Binder, 2014) recommend that a limited number of GHST agents should be used after an overnight fast in a well standardized GHST protocol. These include arginine (ARG), clonidine, glucagon, insulin, and L-dopa.

Although the insulin tolerance test (ITT) is considered as gold standard GHST also for testing pediatric patients, it is not widely used as duplicate test, because of its inconvenience and safety concerns (a clinical endpoint is hypoglycemia, which is associated with symptoms like tremor, somnolence, tachycardia).

The consensus guidelines of the GH Research Society state that the combination of GHRH and ARG as GHST was considered of value in the diagnosis of GHD in childhood and adulthood, provided appropriate cut-off limits were applied (GHRS, 2000). This combination was shown to have high sensitivity and high specificity in children and adolescents (Maghnie, 2002), in late adolescents and young adults (Corneli, 2007). In this latter trial, the cut-off limits were established in lean patients only. Considering that GH secretion is a function of weight and adiposity (Colao, 2009), cut-off limits appropriate for overweight and obese pediatric patients (taking into account age, BMI and waist circumference) remain to be defined.

In a child with clinical criteria for GHD, a peak GH concentration below 10 µg/L has traditionally been used to support the diagnosis. Sensitivity, specificity and GH cut-off values used for different GHSTs in different studies have recently been reviewed (van Vught, 2009).

On this background, various GHSTs are being used in clinical practice, and the requirement for two GHSTs as part of the standard diagnostic procedures is variably being met, either by repetition of the same GHST or by serial performance of two different GHSTs.

These two GHSTs are conducted either on the same day or on two consecutive days, and they require 4 to 6 blood samples per test. This amount of blood taken is considered a safety concern, especially in small children, and safe volume limits are to be respected as, for example, recommended by the WHO (Howie 2011). Apart from this safety factor, it is to be recognized that performing two tests is time- and resource-consuming, and that the associated burden for the children and their parents as well as for the pediatric endocrinologist is high.

Therefore, there exists an urgent need for a new and improved GHST method with desirable features such as a single-test format instead of two tests, proven safety, tolerability, easy application, strong test characteristics on sensitivity and specificity, and reliable repeatability. The present invention fulfills this and related needs.

BRIEF SUMMARY OF THE INVENTION

The presented invention provides a method for measuring growth hormone (GH) levels in children, including a method for diagnosing pituitary-related GH deficiency in children, after single oral administration of macimorelin to children being tested for the condition. Thus, in a first aspect, this invention provides a method for measuring growth hormone levels in children. The method includes the following steps: (a) orally administering to a child being tested an effective amount of macimorelin; and (b) measuring growth hormone level in two, three, or four samples. Two samples are taken from the child at about 30 minutes (e.g., 30±5 min) after step (a) and at about 45 minutes (e.g., 45±5 min) after step (a); three blood samples taken from the child at about 30 minutes (e.g., 30±5 min) after step (a), at about 45 minutes (e.g., 45±5 min) or at about 60 minutes (e.g., 60±5 min) after step (a), and at about 60 minutes (e.g., 60±5 min) or at about 90 minutes (e.g., 90±5 min) after step (a), or four blood samples taken from the child at about 30 minutes (e.g., 30±5 min) after step (a), at about 45 minutes (e.g., 45±5 min) after step (a), at about 60 minutes (e.g., 60±5 min) after step (a), and at about 90 minutes (e.g., 90±5 min) after step (a). The method requires taking no additional blood samples are taken from the child.

In some embodiments, the blood samples are serum or plasma samples. In some embodiments, the blood samples are whole blood samples. In some embodiments, the child is orally administered about 1 mg per kg bodyweight of macimorelin in step (a) of the method. In some embodiments, the two blood samples are taken from the child at about 30 minutes and at about 45 minutes after step (a). In some embodiments, the three blood samples are taken from the child at about 30 minutes, at about 45 minutes, and at about 60 minutes after step (a). In some embodiments, the three blood samples are taken from the child at about 30 minutes, at about 45 minutes, and at about 90 minutes after step (a). In some embodiments, the three blood samples are taken from the child at about 30 minutes, at about 60 minutes, and at about 90 minutes after step (a). In some embodiments, the four blood samples are taken from the child at about 30 minutes, at about 45 minutes, at about 60 minutes, and at about 90 minutes after step (a).

In some embodiments, the method further includes a step (c), after step (b), of comparing the highest growth hormone level (or peak level) in the blood samples obtained in step (b) with a predetermined threshold value. In some cases, the threshold value is determined, for example, based on the age and/or gender of the child being tested. In some embodiments, the predetermined threshold value is about 17 ng/ml. In some embodiments, in step (a) the macimorelin is administered in a composition comprising saccharin, for example, the composition comprises 3.5% macimorelin (calculated as free base), 93.1% spray-dried lactose monohydrate, 2.0% Type A crospovidone, 0.1% colloidal silicon dioxide, 1.0% sodium stearyl fumarate, and 0.3% saccharin sodium dihydrate.

In some embodiments, the method of this invention further includes a step (d), subsequent to step (c), of determining the child, whose highest growth hormone level in the blood samples obtained in step (b) is lower than the predetermined threshold level, as having growth hormone deficiency, and, in the alternative, determining the child, whose highest growth hormone level in the blood samples obtained in step (b) is no lower than the predetermined threshold level, as having no growth hormone deficiency. In some embodiments, a further step (e) is included in the method of treating the child who has been determined in step (d) as having growth hormone deficiency by administering to the child an effective amount of a therapeutic agent for growth hormone deficiency, for example, by way of injection of synthetic human growth hormone.

In a second aspect, the present invention provides a method for treating GHD in children. The method includes the following steps: (1) selecting a child who has been determined as having growth hormone deficiency by the method of this invention; and (2) administering to the child an effective amount of a therapeutic agent for growth hormone deficiency. More specifically, in step (1) the child has been tested by the following procedure: he has been orally administered an effective amount of macimorelin; his growth hormone levels are then measured in two blood samples taken at about 30 minutes after step (a) and at about 45 minutes after step (a), or three blood samples taken at about 30 minutes after step (a), at about 45 minutes or at about 60 minutes after step (a), and at about 60 minutes or at about 90 minutes after step (a), or four blood samples taken at about 30 minutes after step (a), at about 45 minutes after step (a), at about 60 minutes after step (a), and at about 90 minutes after step (a), with no additional blood sample is taken; lastly he is determined to have growth hormone deficiency, if his peak growth hormone level in the blood samples is lower than the predetermined threshold level.

In some embodiments, the child is orally administered about 1 mg per kg bodyweight of macimorelin, and wherein the predetermined threshold value is about 17 ng/ml. The child may be of either gender (boy or girl) or in any age range (pre-pubertal or pubertal). In some embodiments, step (2) of administration of an effective amount of a therapeutic agent for growth hormone deficiency comprises injection of synthetic human growth hormone to the child.

DEFINITIONS

Figure 1:
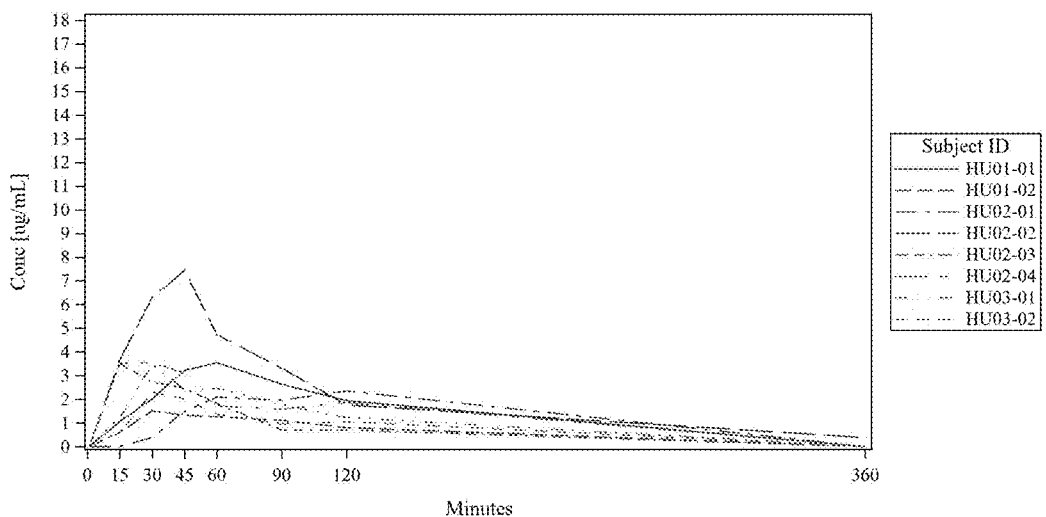
FIG. 1. Individual macimorelin concentration versus time by Cohort, Linear Scale (N=24).
Figure 1:
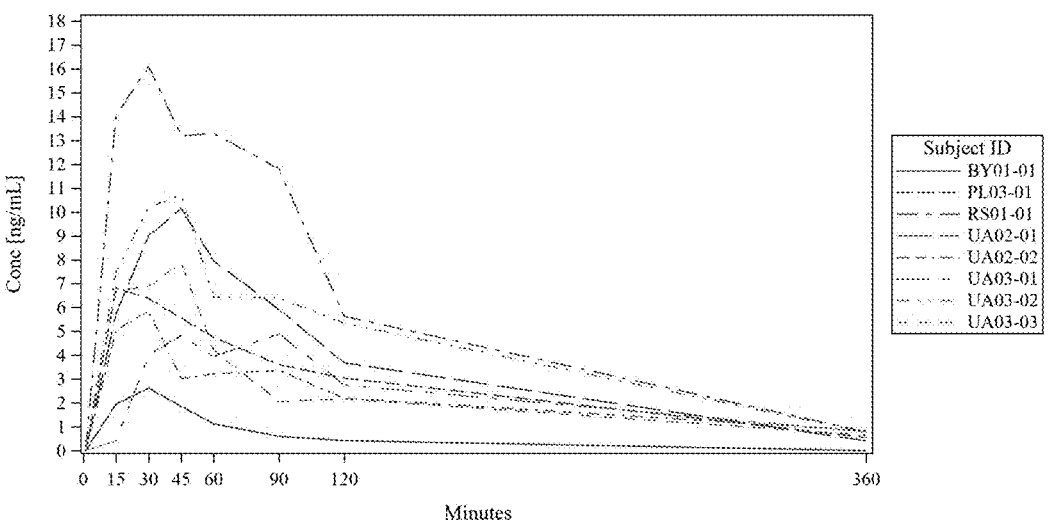
Figure 1:
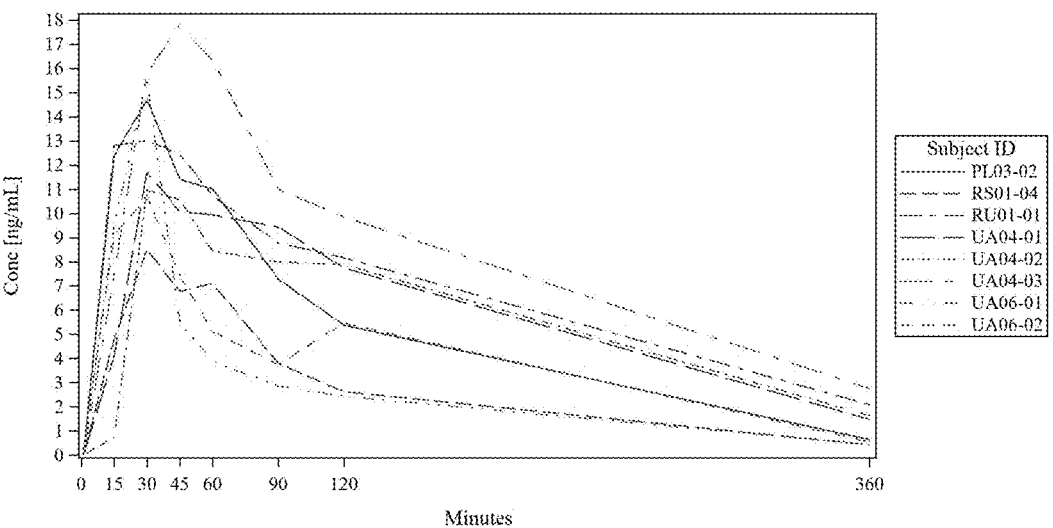

As used herein, a "human child" is a juvenile human of either gender (a male or a female) under the age of 18 years, for example, between the age of about 2 or 3 and about 5, 8, 10, 12, 15, or 17 years, about 5 or 6 and about 10, 12, or 15 years, or about 7 or 8 and about 10 or 12 years. "Children" as used herein include boys and girls that are pre-puberty, e.g., in the age range of about 2 or 3 to about 10 years old, and those that are in puberty, e.g., in the age range of about 11 or 12 to about 15 or 16 years old.

As used herein, "macimorelin" refers to a peptidomimetic compound acting as the ghrelin receptor agonist with growth hormone secretagogue (GHS) activity. Its chemical structure and use in the treatment of GHD are disclosed in U.S. Pat. No. 6,861,409, WO 01/96300, and WO 2007/093820.

As used herein, the term "effective amount" refers to an amount of a given substance that is sufficient in quantity to produce a desired effect. For example, an effective amount of macimorelin for inducing growth hormone secretion in a recipient is an amount of the compound capable to achieve a detectable increase in the secretion of growth hormone upon its administration to the recipient. Any given amount of macimorelin can be determined by routine testing as to whether or not it is an effective amount for stimulating growth hormone secretion. An effective amount of macimorelin is in the range of from about 0.01, about 0.02, about 0.05, about 0.10, to about 0.20 mg per kg bodyweight of recipient at the low-end, and from about 1, about 2, about 5, about 10, about 20, about 25, to about 50 mg/kg bodyweight at the high-end, or within a range defined by any one of the low-end amounts and any one of the high-end amounts, e.g., from about 0.20 to about 2 mg/kg body weight, or about 0.5 mg/kg bodyweight. Typically, an effective amount of macimorelin is in the range of from about 0.8 to about 0.9 mg per kg bodyweight of the subject at the low-end, and from about 1.0, about 1.1 to about 1.2 kg bodyweight of the subject at the high-end, or within a range defined by any one of the low-end amounts and any one of the high-end amounts, for instance, from about 0.9 to about 1.1 mg/kg bodyweight. An effective amount of macimorelin can also be a single value, e.g., of about 0.8, about 0.9, about 1.0, about 1.1 or about 1.2 mg/kg bodyweight. Bodyweight (recorded in kg) may preferably be rounded to the closest integer. For example, about 1.0 mg per kg subject bodyweight of macimorelin is administered to a subject undergoing testing by the method of this invention.

The term "treat" or "treating," as used in this application, describes to an act that leads to the elimination, reduction, alleviation, reversal, or prevention or delay of onset or recurrence of any symptom of a relevant condition. In other words, "treating" a condition encompasses both therapeutic and prophylactic intervention against the condition.

The term "test" and "testing," as used in this application, describes to an act that leads to the clarification of a suspected presence of a specific condition based on a subject's symptoms and to the identification of the condition as being present or absent. In other words, "testing" for a condition encompasses the confirmation or exclusion of the condition being present in a test subject.

As used herein, the term "blood sample" encompasses a whole blood sample as well as a fraction of whole blood such as serum or plasma sample. Whenever two or more "blood samples" are used for testing in the same method scheme, these "blood samples" are of the same type: for example, if the first sample is serum, then the second and any subsequent samples are also serum.

The term "about" as used herein denotes a range of +/−10% of a reference value. For examples, "about 10" defines a range of 9 to 11.

The term "consisting essentially of" and its grammatical variations are used herein to describe the nature of a composition being exclusive of unnamed active ingredients while inclusive of unnamed inactive ingredients. For example, a composition that is characterized as "consisting essentially of" macimorelin and one or more physiologically/pharmaceutically acceptable excipients or carriers and suitable for use in the claimed method of this invention does not contain any additional ingredient having any detectable effect on the functionality of macimorelin relevant to the method but may contain additional ingredients having no detectable effect on the relevant activity of macimorelin.

DETAILED DESCRIPTION OF THE INVENTION

I. Introduction

Growth hormone deficiency (GHD) in children is a rare, aetiologically diverse condition that results in growth failure and short stature. Inadequate response to two different growth hormone stimulation tests (GHST) is required for the diagnosis of GHD. Macimorelin acetate, a potent, orally administered growth hormone (GH) secretagogue, is approved by the FDA and EMA for the diagnosis of adult GHD. This study (AEZS-130-P01) is designed to investigate the characteristics of macimorelin acetate as a diagnostic test in children with suspected GHD.

This was an open-label, group comparison, dose escalation trial to investigate the safety, tolerability, pharmacokinetics and pharmacodynamics of single-dose 0.25, 0.5, and 1 mg/kg oral macimorelin acetate in paediatric subjects with suspected GHD. The macimorelin GHST was administered between two standard GHST, conducted as per local clinical practice, with a recovery period of 7-28 days between tests. For the purposes of obtaining a detailed macimorelin PK profile in children, blood samples were collected pre-dose (±15 min) and 15, 30, 45, 60, 90, 120, and 360 minutes after macimorelin acetate intake.

Overall, 24 pediatric subjects (8 per cohort [C1, C2, C3]) were included in the pharmacokinetic/pharmacodynamic (PK/PD) analysis. Five males and 3 females were observed in C1 and C2, 7 males and 1 female in C3. In all three cohorts, at least 3 subjects represented Tanner stages I or II. All 24 subjects (100%) were white, with a median age of 9.8, 9.0 and 10.5 years (range 4-15 years) and a median body-mass index of 16.1 kg/m$^2$ (12.4-21.4 kg/m$^2$) at screening. Overall, 88 adverse events were reported, many related to the standard GHST; none were considered related to the macimorelin test. Maximum plasma concentrations for macimorelin were mainly observed between 30-45 min. The mean $C_{max}$ values were 3.46, 8.13 and 12.87 ng/ml for C1, C2, and C3, respectively. The AUCs increased with dose; the mean $AUC_{0-6}$ values were 6.69, 18.02 and 30.92 h*ng/mL. The mean elimination half-lives were 1.22, 1.61 and 1.71 h, respectively. PK and PD profiles for all three cohorts were comparable, with peak GH levels mainly observed within 30-60 min following macimorelin intake.

Macimorelin acetate was safe and well tolerated in all dosing cohorts. A dose-dependent increase in macimorelin $C_{max}$ and AUC in children and adolescents correlated well with data from adult subjects. A robust dose-proportional GH response was also achieved. PD results showed that GH response was comparable in all dose groups, with a slight shift to earlier $t_{max}$ at higher macimorelin doses. Finally, the outcome of the macimorelin GHST showed a surprisingly high agreement with the outcome of the two standard GHSTs as well as the final diagnose as assessed by the Principal Investigator. In C3, GH secretion was stimulated evidently in all 8 patients. Finally, the outcome of the macimorelin GHST applied as a single test showed agreement with the outcome of the combination of the two sGHSTs as well as with the PI assessment in 7 of 8 subjects.

II. Assessing Growth Hormone Levels and Growth Hormone Deficiency (GHD)

One aspect of this invention is to provide a method in the single test format for measuring growth hormone levels in children and for detecting GHD in children. A single test format GHD test has not been available prior to this invention. This new method not only reduces the burden on test administrators and test subjects by reducing the test time duration and number of blood draws but also provides reliable and superior diagnostic performance as a stand-alone test, without the need for the conduct of a second test.

Children who exhibit certain clinical features such as short or small stature (e.g., within the lowest 5 percentile of height/weight in an age group), low growth rate for age and pubertal stage, increased amount of fat around the waist, younger appearance than age, and delayed tooth development may be suspected of suffering from growth hormone deficiency. The method of this invention can be used to assess their peak growth hormone level following stimulation and thus determine whether or not the condition of growth hormone deficiency is present. In some cases, the child being tested is a pre-pubertal boy or girl, i.e., younger than about 10 years of age, for example, from about 2 or 3 to about 10 years of age, or from about 3 or 4 to about 8 or 10 years of age, or from about 5 or 6 to about 8 or 10 years of age. In the alternative, the child being tested is a pubertal boy or girl, i.e., older than about 11 years old but younger than about 15 or 16 years of age, for example, from about 11 or 12 to about 15 or 16, or from about 13 or 14 to about 15 or 16 years of age.

One main feature of the growth hormone testing method of this invention is the single stimulation test format in contrast to the standard two-test format currently in use by medical professionals. Rather than having two separate tests, which are performed at least one day apart and involve as many as 10 blood draws, the new method of this invention requires only one test and as few as only 2/no more than 4 blood draws in order to achieve reliable diagnostic performance in accuracy, specificity, and sensitivity for detecting growth hormone deficiency, thus greatly reducing the testing burden and potential harm to the children being tested.

Specifically, the method of the present invention has achieved such significant improvement by introducing macimorelin as test on diagnosing GHD in children, using macimorelin in a higher macimorelin dose than required in adult, and a higher threshold value for diagnosing growth hormone deficiency than being used in standard GHSTs. While the conventional dose of macimorelin used in current practice, especially when adult patients are tested for GHD, is 0.5 mg/kg patient body weight, the present inventors have unexpectedly discovered that better diagnostic performance can be achieved when a higher dose of macimorelin is used in the growth hormone stimulation test for children: for example, a macimorelin dose of 1 mg/kg body weight has been found to very effectively stimulate GH secretion and thus indicate GHD in the one-test method of this invention.

In some embodiments, macimorelin is administered to the child being tested in a composition comprising macimorelin and optionally further pharmaceutically acceptable excipients, such as carrier substances. Preferably, the macimorelin is administered in a composition comprising macimorelin and sweetener. A suitable sweetener is, for example, saccharin. Advantageously, saccharin was found to be a suitable taste masking agent for the bitter taste of macimorelin.

In some embodiments, macimorelin is administered in a composition comprising about 2.0 to about 5.0% (w/w) macimorelin calculated as free base, about 90.0 to about 96.0% (w/w) spray-dried lactose monohydrate, about 1.0 to about 3.0% (w/w) crospovidone Type A, 0.05 to about 0.5% (w/w) colloidal silicon dioxide, about 0.5 to about 2.0% (w/w) sodium stearyl fumarate, and 0.05 to about 0.5% w/w saccharin sodium dihydrate. For example, the composition comprises about 3.5% (w/w) macimorelin (calculated as free base), about 93.1% (w/w) spray-dried lactose monohydrate, about 2.0% (w/w) crospovidone Type A, about 0.1% (w/w) colloidal silicon dioxide, about 1.0% (w/w) sodium stearyl fumarate, and about 0.3% (w/w) saccharin sodium dihydrate.

Moreover, for diagnostic purpose, the one-test method of this invention utilizes a much higher threshold growth hormone level to indicate adequate response to macimorelin stimulation: instead of the 2.8 ng/mL cutoff value commonly used in adult tests and the 7-10 ng/mL cutoff value as commonly used in standard GHSTs in children, the threshold used in the method of the present invention is in a higher range of about 10-20 ng/mL: over about 10 ng/mL (e.g., over 10 or 10.5 ng/mL), about 11 ng/mL (e.g., over 11 or 11.5 ng/mL), about 12 ng/mL (e.g., over 12 or 12.5 ng/mL), about 13 ng/mL (e.g., over 13 or 13.5 ng/mL), about 14 ng/mL (e.g., over 14 or 14.5 ng/mL), about 15 ng/mL (e.g., over 15 or 15.5 ng/mL), about 16 ng/mL (e.g., over 16 or 16.5 ng/mL), about 17 ng/mL (e.g., over 17 or 17.5 ng/mL), about 18 ng/mL (e.g., over 18 or 18.5 ng/mL), about 19 ng/mL (e.g., over 19 or 19.5 ng/mL), about 20 ng/mL (e.g., over 20 or 20.5 ng/mL). In some cases, the cutoff value is further chosen based on test subject's age range (e.g., any of those stated in this disclosure) and/or gender (whether the child is a boy or a girl) and/or Body Mass Index (BMI, for instance, whether the child's BMI is or is not greater than about 25, or whether the child's BMI is or is not greater than about 30) to optimize diagnostic performance of the method of this invention.

In combination with the use of a higher macimorelin dosing and higher growth hormone threshold level, the one-test method of this invention requires far fewer blood draws, thus providing a further desirable feature of the new test. Specifically, after oral administration of macimorelin, blood is drawn from the child at least twice but no more than four time during the time period of about 90 minutes with an interval of about 15 to 30 minutes. For instance, two blood draws may be performed at about 30 minutes and at about 45 minutes after macimorelin administration. In another example, three blood draws may be performed at about 30 minutes, at about 45 minutes (or at about 60 minutes), and then at about 60 minutes (or at about 90 minutes) after macimorelin administration. In a further example, four blood draws may be performed at about 30 minutes, at about 45 minutes, at about 60 minutes, and at about 90 minutes after macimorelin administration). If the peak level, i.e., the highest level among all of the growth hormone levels detected in all of the blood samples is found to be lower than a predetermined threshold level, then the child being tested is deemed to have a condition of growth hormone deficiency. Conversely, if the highest level is higher than or equal to the threshold level, then the child is deemed to have no growth hormone deficiency. Once the determination is made, the child being test is optionally subject to appropriate treatment as prescribed by the attending physician.

In practicing the method of this invention, different types of blood samples may be used: for example, serum or plasma samples are used in some cases whereas whole blood samples are used in other cases.

III. Treatment Methods

Another aspect of the present invention relates to the treatment of children who have been identified as suffering from growth hormone deficiency as determined by the method described herein. The most common treatment for GHD children is administration of synthetic human growth hormone—known as somatotropin—typically by injection on a regular basis, e.g., daily or once every other day.

Thus, this invention provides a treatment method for ameliorating the symptoms of growth hormone deficiency in a child. The method includes at least two steps: a first step of selecting a child suitable for receiving treatment for GHD, a child who has been orally administered an effective amount of macimorelin (e.g., 1 mg/kg body weight), who then has had 2-4 blood draws (but no more) at the time intervals of about 15-30 minutes within the time period of about 90 minutes after macimorelin administration (e.g., two blood draws at 30±5 minutes and at 45±5 minutes after macimorelin administration; or three blood draws at 30±5 minutes, at 45±5 minutes, and at 60±5 or 90±5 minutes after macimorelin administration; or four blood draws at 30±5 minutes, at 45±5 minutes, at 60±5 minutes, and at 90±5 minutes after macimorelin administration), and whose growth hormone levels in all of the blood samples have been found to be lower than a predetermined threshold level (e.g., about 17 ng/mL).

The second step of the method is to administer to a child so selected in the first step a therapeutic agent effective for treating children suffering from growth hormone deficiency, for example, recombinant human growth hormone via regular injection.

On the other hand, if a child who was suspected of suffering from growth hormone deficiency (e.g., due to exhibiting certain clinical characteristics such as retarded growth including shorter stature and underdeveloped musculature) but has been determined by the method of this invention as having no growth hormone deficiency, the child may receive alternative treatment, if any, and as deemed appropriate by the attending physician. For example, since being very short (e.g., due to a late puberty) can negatively affect a child's self-esteem, a mental health counselor or psychologist can provide counselling for the child. Furthermore, well-being programs can be employed to improve a child's sleeping habits and to better serve his dietary needs (e.g., including a diet fortified with proteins and vitamins etc.) as well as to incorporate routine physical exercises into a healthy lifestyle.

EXAMPLES

The following examples are provided by way of illustration only and not by way of limitation. Those of skill in the art will readily recognize a variety of non-critical parameters that could be changed or modified to yield essentially the same or similar results.

SUMMARY

Macimorelin is a potent, orally active growth hormone secretagogue (GHS) that has been used for GHD testing, in particular, by measuring the stimulated GH level after oral administration. See, e.g., Macimorelin as a compound and its use in treatment of GHD has been disclosed by Martinez et al. in WO 01/96300 A1 as well as in U.S. Pat. No. 8,192,719. A poster titled "Validation of Macimorelin As a Diagnostic Test for Adult Growth Hormone Deficiency (AGHD): A Phase 3 Study in Comparison with the Insulin Tolerance test (ITT)" was presented by Garcia et al. on the 99th Annual Meeting of the Endocrine Society in 2017, reporting details of the clinical study in adults. In the adult indication, macimorelin has confirmed to be a safe, reliable, easy to use test on GHD with strong characteristics on sensitivity and specificity as well as repeatability. Garcia et al. (*J. Clin. Endocrin. Metab.* Apr. 4, 2013, 1157), Garcia et al. (*J. Clin. Endocrinol. Metab.* May 31, 2018-00665), WO2007/093820, and U.S. Pat. No. 10,288,629 are among other publications describing the use of macimorelin in the diagnosis of GHD.

In the pediatric indication, macimorelin has been investigated in one clinical study AEZS-130-P01 (Study P01') on safety, tolerability, pharmacokinetic (PK) and pharmacodynamic (PD: GH levels) of macimorelin. Study P01 is a study as being defined in the clinical development plan and as being agreed with the FDA as well as the EMA.

The main features of Study P01 are summarized as follows:

Sequential cohorts of trial participants received macimorelin at ascending single oral doses: 0.25 mg/kg body weight in Cohort 1 (C1), 0.5 mg/kg body weight in Cohort 2 (C2), and 1 mg/kg body weight in Cohort 3 (C3).

For determination of macimorelin PK/PD: blood sampling at pre-dose, then 15, 30, 45, 60, 90, 120, and 360 minutes after the administration of macimorelin.

Two standard GHSTs (sGHSTs) had to be performed in a patient according to local practice. The related sGHST agents were considered as 'background' and not as IMPs. (Accepted test agents: insulin (insulin tolerance test or ITT), arginine, arginine/growth hormone releasing hormone (GHRH), clonidine, glucagon, L-dopa).

Results

In total, 24 patients were administered the macimorelin test, with 8 patients in each of the three dosing cohorts (C1, C2, and C3). At screening, the median parameters for all three dosing cohorts were for age 10.5 years (range: 4-15 years), height 123.35 cm (range: 46.0-152.5 cm), weight 25.5 kg (range: 12-43 kg) and body mass index (BMI) 16.1 $kg/m^2$ (range: 12.4-21.4 $kg/m^2$).

a) Results of the Exploratory Analyses for the GH Cut-Off Point:

Peak GH values by GHD diagnosis were compared based on GHST results and investigator's assessment. Diagnostic characteristics of GH values (i.e., sensitivity, specificity, and Youden indices (non-weighted, weighted)) tested as cut-off points were listed with the most solid expression of diagnostic characteristics to be noted for C1 at a peak GH of 10.03 ng/mL, for C2 at a peak GH of 10.43 ng/mL, and for C3 at 17.13 ng/mL.

The diagnostic outcome of the GHSTs is presented in Table 2. In this table, the diagnostic outcome of the sGHST if considered as 'confirmed' if both sGHSTs are available and both resulted in a peak GH≤7 ng/mL or 'not confirmed' of at least one of the peaks is above 7 ng/mL. The outcome 'not confirmed' is categorized to 'excluded' if both sGHST results are available and the GH peaks are above 7 ng/ml, and to 'equivocal' if the case does not fit to any of the above described. The investigator's assessment is based on local diagnostic standard practice. The macimorelin GHST was tested against a cut-off point calculated from the individual peak GH values.

TABLE 1

Diagnostic Outcome of GHSTs (Number of Subjects = 24)

| Cohort | Cut-off GH for Macimorelin GHST (ng/mL) | Patient | Peak GH (ng/mL) after Macimorelin GHST | Macimorelin GHST | Investigator's assessment | sGHSTs |
|---|---|---|---|---|---|---|
| C1 | 10.030 | HU01-01 | 8.38 | Confirmed | Not Confirmed | Not Confirmed (Equivocal) |
| | | HU01-02 | 8.61 | Confirmed | Confirmed | Not Confirmed (Equivocal) |
| | | HU02-01 | 0.51 | Confirmed | Not Confirmed | Not Confirmed (Equivocal) |
| | | HU02-02 | 21.73 | Not Confirmed | Not Confirmed | Not Confirmed (Excluded) |
| | | HU02-03 | 5.22 | Confirmed | Confirmed | Not Confirmed (Equivocal) |
| | | HU02-04 | 10.03 | Confirmed | Confirmed | Confirmed |
| | | HU03-01 | 14.07 | Not Confirmed | Not Confirmed | Not Confirmed (Excluded) |
| | | HU03-02 | 9.78 | Confirmed | Not Confirmed | Not Confirmed (Equivocal) |

TABLE 1-continued

Diagnostic Outcome of GHSTs (Number of Subjects = 24)

| Cohort | Cut-off GH for Macimorelin GHST (ng/mL) | Patient | Peak GH (ng/mL) after Macimorelin GHST | Macimorelin GHST | Investigator's assessment | sGHSTs |
|---|---|---|---|---|---|---|
| C2 | 10.430 | BY01-01 | 5.06 | Confirmed | Confirmed | Not Confirmed (Excluded) |
| | | PL03-01 | 20.73 | Not Confirmed | Not Confirmed | Not Confirmed (Excluded) |
| | | RS01-01 | 7.41 | Confirmed | Confirmed | Confirmed |
| | | UA02-01 | 10.43 | Confirmed | Confirmed | Confirmed |
| | | UA02-02 | 21.36 | Not Confirmed | Not Confirmed | Not Confirmed (Excluded) |
| | | UA03-01 | 16.41 | Not Confirmed | Not Confirmed | Not Confirmed (Excluded) |
| | | UA03-02 | 9.67 | Confirmed | Confirmed | Confirmed |
| | | UA03-03 | 27.42 | Not Confirmed | Confirmed | Confirmed |
| C3 | 17.130 | PL03-02 | 17.13 | Confirmed | Confirmed | Confirmed |
| | | RS01-04 | 14.46 | Confirmed | Confirmed | Confirmed |
| | | RU01-01 | 59.73 | Not Confirmed | Not Confirmed | Not Confirmed (Excluded) |
| | | UA04-01 | 49.16 | Not Confirmed | Not Confirmed | Not Confirmed (Equivocal) |
| | | UA04-02 | 25.07 | Not Confirmed | Not Confirmed | Not Confirmed (Excluded) |
| | | UA04-03 | 14.63 | Confirmed | Not Confirmed | Not Confirmed (Equivocal) |
| | | UA06-01 | 11.35 | Confirmed | Confirmed | Confirmed |
| | | UA06-02 | 44.73 | Not Confirmed | Not Confirmed | Not Confirmed (Equivocal) |

Based on the considerations outlined above, Table 2 is presenting agreement between principal investigator's (PI's) assessment and outcome of both sGHSTs: in 21 (87.5%) patients (i.e., 8 confirmed and 13 not confirmed) there is an agreement between investigators assessment and sGHST outcomes. In 3 (12.5%) patients investigator concluded GHD, while sGHSTs excluded (in 1 patient) the diagnosis or were equivocal (in 2 patients).

Furthermore, the diagnostic results can be summarized as following (Table 2): the macimorelin GHST shows 'GHD not confirmed' only in 1 (9.09%) patient in C2 from overall 11 patients assessed as 'GHD' by the investigator in all three cohorts.

From a total of 13 patients assessed by the investigator as 'not confirmed' of having GHD, the macimorelin GHST confirmed GHD in 3 (23.08%) patients in C1 and in 1 (7.69%) patient in C3, respectively.

TABLE 2

Summary of Diagnostic Results of Macimorelin GHST vs. sGHST and vs. Investigator's Assessment

| | | PI's Assessment | | sGHST | |
|---|---|---|---|---|---|
| | Macimorelin GHST | GHD (N = 11) | Non GHD (N = 13) | Confirmed (N = 8) | Not Confirmed (N = 16) |
| Cohort 1 | Confirmed, n (%) | 3 (27.27%) | 3 (23.08%) | 1 (12.50%) | 5 (31.25%) |
| | Not Confirmed, n (%) | 0 | 2 (15.38%) | 0 | 2 (12.50%) |
| | Total, n (%) | 3 (27.27%) | 5 (38.46%) | 1 (12.50%) | 7 (43.75%) |
| Cohort 2 | Confirmed, n (%) | 4 (36.36%) | 0 | 3 (37.50%) | 1 (6.25%) |
| | Not Confirmed, n (%) | 1 (9.09%) | 3 (23.08%) | 1 (12.50%) | 3 (18.75%) |
| | Total, n (%) | 5 (45.45%) | 3 (23.08%) | 4 (50%) | 4 (25%) |
| Cohort 3 | Confirmed, n (%) | 3 (27.27%) | 1 (7.69%) | 3 (37.50%) | 1 (6.25%) |
| | Not Confirmed, n (%) | 0 | 4 (30.77%) | 0 | 4 (25%) |
| | Total, n (%) | 3 (27.27%) | 5 (38.46%) | 3 (37.50%) | 5 (31.25%) |

Considering the data presented above, strongest test characteristics for the macimorelin test is observed in C3: GH secretion was stimulated evidently in all 8 patients. Finally, the outcome of the macimorelin GHST applied as a single test showed agreement with the outcome of the combination of the two sGHSTs as well as with the PI assessment in 7 of 8 subjects.

b) Results on PK/PD in Summary:

Overall, the macimorelin PK and PD of C1, C2, and C3 show comparable profiles:

the macimorelin $T_{max}$ is comparable for all three groups, with mean Tmax values of about 0.5-0.75 h;

the mean macimorelin $C_{max}$ shows a dose-proportional increase;

the AUC increases with the macimorelin dose;

maximum GH release is observed at 0.25-2 h after macimorelin administration, with mean $T_{max}$ values at about 0.5-1 h.

Macimorelin plasma concentrations showed a dose-dependent increase with high inter-individual variability (cf. FIG. 1).

Maximum values for AUC and $C_{max}$ are observed in C3 at a macimorelin dosing of 1.0 mg/kg body weight, which is double the dose as used in the adult indication.

Figure 2:
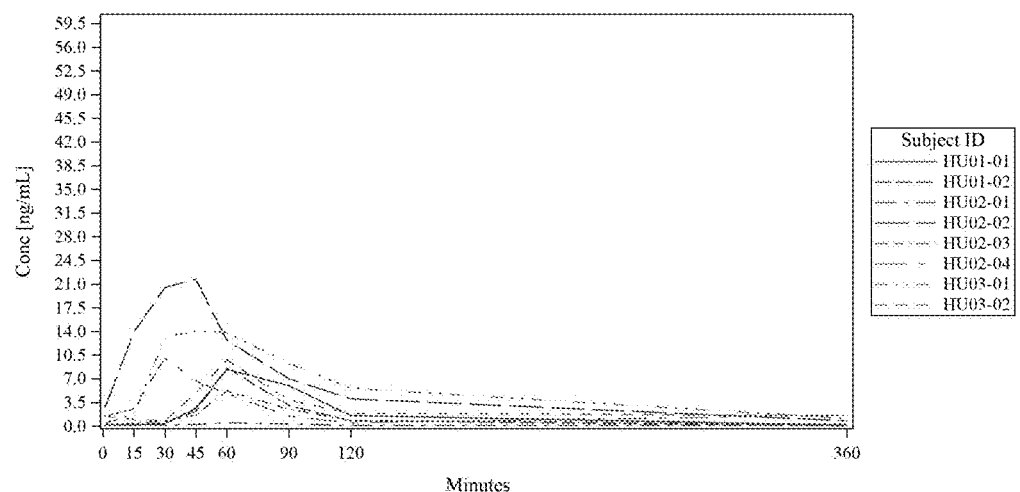
FIG. 2. Individual GH concentration after macimorelin GHST versus time, Linear Scale (N=24).
Figure 2:
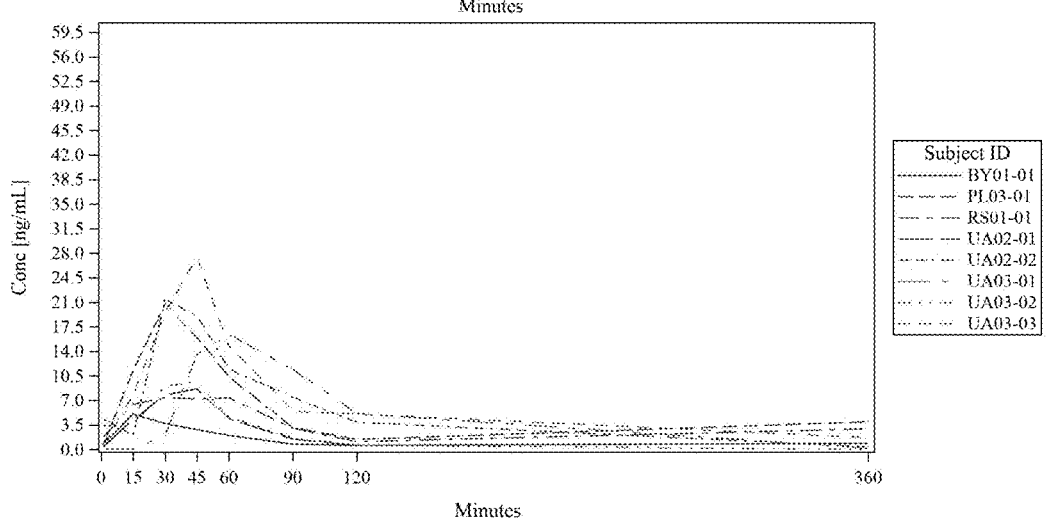
Figure 2:
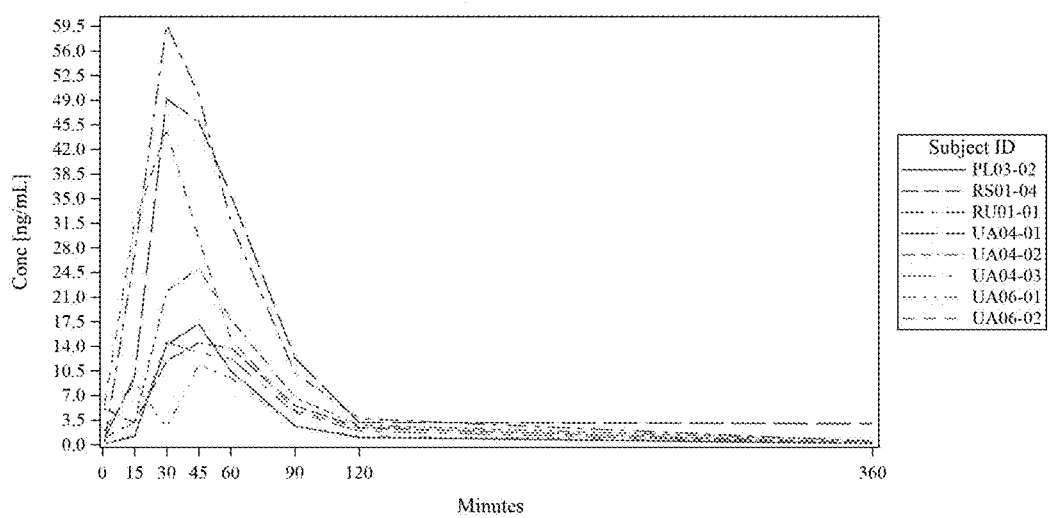

GH concentration is increasing following macimorelin administration with a tendency to higher values with ascending dose (cf. FIG. 2). Following macimorelin administration peak GH levels were observed in C1 within 0.5-1 h (mean $T_{max}$ at 52.5 min (SD 11.3)), in C2 within 0.25-1 h (mean $T_{max}$ 37.5 min (SD 13.9)), and in C3 within 0.5-0.75 h (mean $T_{max}$ 37.5 min (SD 8.0)).

Figure 3:
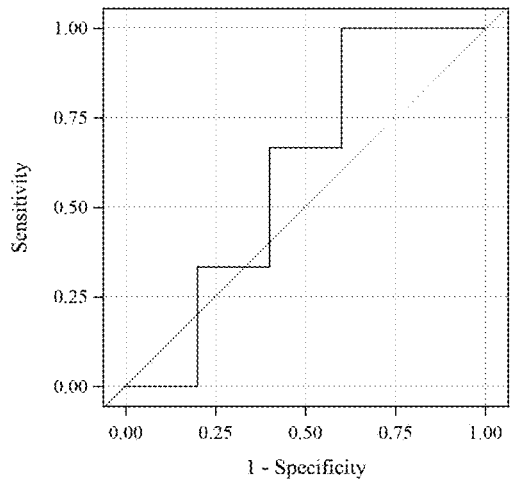
FIG. 3. Receiver Operating Characteristic (ROC) curve of macimorelin GHST by Cohort (N=24).
Figure 3:
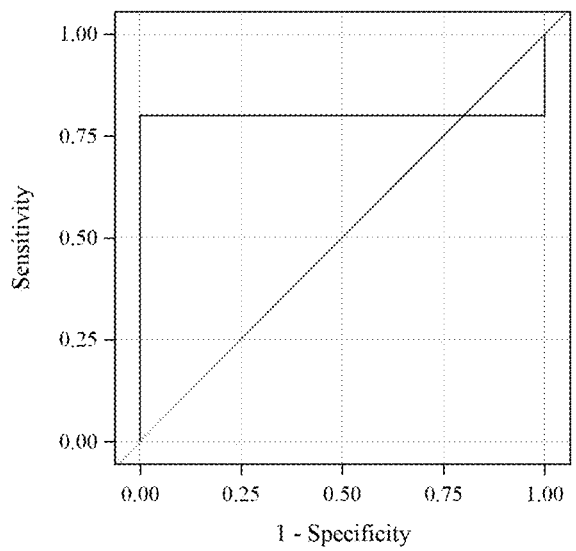
Figure 3:
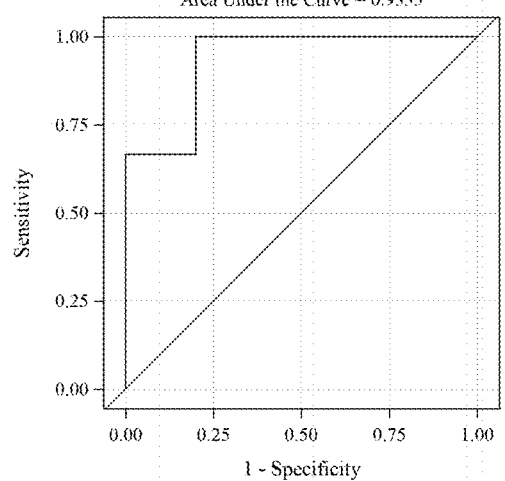

Furthermore, the sensitivity analysis supports the dosing in C3 with strongest test characteristics expressed at a cut-off point of approximately 17 ng/mL GH (cf. FIG. 3), with a specificity of 0.80, a sensitivity of 1.00, a Youden-index of 0.80 and an ROC AUC of 0.933. It is to be underlined that macimorelin showed surprisingly strong test characteristics in C3, with an evident stimulation of GH secretion in all 8 patients. Finally, the outcome of the macimorelin GHST applied as a single test showed agreement with the outcome of the combination of two sGHSTs as well as with the PI assessment in 7 of 8 subjects.

c) Results on Safety/Tolerability

No adverse event was reported in relation to macimorelin. The data obtained from patient questionnaires, safety laboratory data (hematology, clinical chemistry, urinalysis) as well as ECGs (prior to oral macimorelin and at 60 min post-dose) showed excellent safety and tolerability of macimorelin in all three dosing cohorts.

Methodology

Plasma concentrations of macimorelin and serum concentrations of GH were analyzed in central laboratories.

Macimorelin plasma concentrations: the analysis of plasma samples for macimorelin concentration was carried out at a central laboratory, Prolytic GmbH, Germany, using a validated liquid chromatography-mass spectrometry (LCMS/MS) method with a detection limit of 0.2 ng/mL (Franz, 2005).

Preliminary pharmacokinetics (PK) were determined by: time of maximum measured concentration ($t_{max}$) and maximum concentration ($C_{max}$) of macimorelin plasma concentrations in the sampling period.

GH serum concentration: the analysis of serum samples for GH concentration was carried out at a central laboratory by a validated immunochemiluminometric assay (IDS-iSYS Human Growth Hormone (hGH), Immunodiagnostic Systems Ltd [UK]) (Manolopoulou et al., 2012). This assay is standardized to the recombinant growth hormone calibration standard WHO 98/574, and complies with recommendations on assay standardization as outlined by Clemmons (Clemmons, 2011).

The analytical laboratory applied for GH was: Central Laboratory Synevo Łódź, Krakusa Str. 28, 93-515 Łódź. Poland. The lower limit of quantification was <0.05 ng/mL.

CONCLUSION

The data presented above strongly indicate the capability of macimorelin to become a stand-alone test in the diagnosis of GHD in children, capable of replacing current medical standards and thus being introduced in medical guidelines as a sole test required to diagnose GHD.

As shortly outlined above, strongest test characteristics were expressed surprisingly at a macimorelin dose of 1 mg/kg and with at GH cut-off points above 10 ng/mL, e.g., at about 10, 11, 12, 13, 14, 15, 16, or up to about 17 ng/mL. In adults, a macimorelin dose of 0.5 mg/kg is approved by the FDA as well as the EMA, with a cut-off point of 2.8 ng/mL. See, for example, U.S. Pat. No. 10,288,629.

The present Study P01 delivered surprisingly strong outcome results for the macimorelin test in a dosing of 1.0 mg/kg. In the respective cohort, macimorelin achieved an evident stimulation of GH secretion in all 8 patients. Finally, the outcome of the macimorelin GHST applied as a single test showed agreement with the outcome of the combination of two sGHSTs as well as with the PI assessment in 7 of 8 subjects. Therefore, the overall characterization of macimorelin in this first pediatric trial supports the choice of a macimorelin dose of 1.0 mg/kg for the investigation in a Phase 3 study on efficacy (i.e., test validity).

Therefore, the present invention provides a method for measuring growth hormone (GH) levels in children, including a method of assessing pituitary-related GH deficiency in children, after single oral administration of macimorelin to the child:

as a stand-alone test (one test required only);

with two to four blood samples collected in a time period of 90 minutes, in time windows of 15 up to 30 minutes; and with a GH cut-off point in a range of 10.2 ng/mL to 20 ng/mL.

All patents, patent applications, and other publications cited in this application are incorporated by reference in the entirety for all purposes.

REFERENCES

| | |
|---|---|
| Binder 2014 | Binder G (2014). S2e-Leitlinie 174/002 Aktualisierte Leitlinie. Diagnostik des Wachstumshormonmangels im Kindes- und Jugendalter. (Guideline text). AWMF online. |
| Clemmons 2011 | Clemmons DR. (2011, April). Consensus statement on the standardization and evaluation of growth hormone and insulin-like growth factor assays. Clin Chem. 57(4): 555-559. |

| | |
|---|---|
| Colao 2009 | Colao A. (2009, November). A reappraisal of diagnosing GH deficiency in adults: role of gender, age, waist circumference, and body mass index. J. Clin Endocrinol. Metab. 94(11): 4414-4422. |
| Cook 2009 | Cook DM, Yuen KC, Biller BM, Kemp SF, Vance ML; American Association of Clinical Endocrinologists. (2009, Sep-Oct). American Association of Clinical Endocrinologists medical guidelines for clinical practice for growth hormone use in growth hormone-deficient adults and transition patients - 2009 update. Endocr Pract. 15 Suppl 2:1-29. |
| Corneli 2007 | Corneli G (2007, December). Cut-off limits of the GH response to GHRH plus arginine test and IGF-I levels for the diagnosis of GH deficiency in late adolescents and young adults. European J. Endocrinol. 157(6): 701-708. |
| Franz 2005 | Franz A. (2005, July). Partial validation of an HPLC-MS/MS method for the determination of EP01572 in human plasma. Prolytic report EP01572/050000003, Jul 2005. |
| Garcia 2013 | Garcia J, Swerdloff R, Wang C, Kyle M, Kipnes M, Biller B, Cook D, Yuen K, Bonert V, Dobs A, Molitch M, Merriam G. Macimorelin (AEZS-130)-Stimulated Growth Hormone (GH) test: Validation of a Novel Oral Stimulation Test for the Diagnosis of Adult GH Deficiency. J Clin Endocrinol Metab April 2013-1157. |
| Garcia 2017 | Garcia JM, Beverly MKB, Korbonits M, et al. Validation of Macimorelin As a Diagnostic Test for Adult Growth Hormone Deficiency (AGHD): A Phase 3 Study in Comparison with the Insulin Tolerance test (ITT). Poster presented on the 99th Annual Meeting of the Endocrine Society, 2017. |
| Garcia 2018 | Garcia JM, Beverly MKB, Korbonits M, Popovic V, Luger A, Strasburger CJ, Chanson P, Medic-Stojanoska M, Schopohl J, Zakrzewska A, Pekic S, Bolanowski M, Swerdloff R, Wang C, Blevins T, Marcelli M, Ammer N, Sachse R, Yuen KDJ. Macimorelin as a Diagnostic Test for Adult GH Deficiency. J Clin Endocrinol Metab. May 2018-00665. |
| Gharib 2003 | Gharib H. (2003, Jan-Feb). American Association of Clinical Endocrinologists medical guidelines for clinical practice for growth hormone use in adults and children-2003 update. AACE. Endocr Pract. 9(1): 64-76. |
| GHRS 2000 | GHRS. (2000, November). Consensus guidelines for the diagnosis and treatment of growth hormone (GH) deficiency in childhood and adolescence: summary statement of the GH Research Society. J. Clin. Endocrinol. Metab. 85(11): 3990-3993. |
| GHRS 2019 | GHRS (2019, September). Diagnosis, Genetics, and Therapy of Short Stature in Children: A Growth Hormone Research Society International Perspective. Horm Res Paediatr 2019; 92: 1-14 |
| Guzzetti 2019 | Guzzetti C. et al. (2016, May). Cut-off limits of the peak GH response to stimulation tests for the diagnosis of GH deficiency in children and adolescents: study in patients with organic GHD. European J. Endocrinol. (2016) 175, 41-47. |
| Howie 2011 | Howie SRC (2011)). Blood sample volumes in child health research: review of safe limits. Bull World Health Organ 2011; 89: 46-53 |
| Maghnie 2002 | Maghnie M. (2002, February). GHRH plus arginine in the diagnosis of acquired GH deficiency of childhood-onset. J. Clin. Endocrinol. Metab. 87(6): 2740-2744 |
| Manolopoulou 2012 | Manolopoulou J, Alami Y, Petersenn S, Schophol J, Wu Z, Strasburger CJ, Bidlingmaier M. (2012 October). Automated 22-kD growth hormone-specific assay without interference from Pegvisomant. Clin Chem. 58(10): 1446-1456. Epub 20 Aug 2012. |
| Molitch 2011 | Molitch ME, Clemmons DR, Malozowski S, Merriam GR, Vance ML; Endocrine Society. (2011, June). Evaluation and treatment of adult growth hormone deficiency: an Endocrine Society clinical practice guideline. J Clin Endocrinol Metab. 96(6): 1587-1609. |
| Van Vught 2009 | van Vught AJ. (2009, August). Pharmacological and physiological growth hormone stimulation tests to predict successful GH therapy in children. J. Paediatr Endocrinol. Metab. 22(8): 679-694. |

What is claimed is:

1. A method for detecting and treating growth hormone deficiency in a human child, comprising:
   (a) orally administering to the child about 1 mg per kg bodyweight of macimorelin;
   (b) measuring growth hormone level in
      (i) two blood samples taken from the child at about 30 minutes after step
         (a) and at about 45 minutes after step (a), or
      (ii) three blood samples taken from the child at about 30 minutes after step
         (a), at about 45 minutes after step (a), and at about 60 minutes after step (a),
   and wherein no additional blood sample is taken from the child;
   (c) comparing highest growth hormone level in the blood samples obtained in step (b) with a predetermined threshold value of about 17 ng/ml;
   (d) determining the child, whose highest growth hormone level in the blood samples obtained in step (b) is lower than the predetermined threshold value, as having growth hormone deficiency, and determining the child, whose highest growth hormone level in the blood samples obtained in step (b) is no lower than the predetermined threshold value, as having no growth hormone deficiency; and (e) injecting into the child who has been determined in step (d) as having growth hormone deficiency an effective amount of a synthetic human growth hormone.

2. The method of claim 1, wherein the blood samples are serum samples.

3. The method of claim 1, wherein the blood samples are plasma samples.

4. The method of claim 1, wherein the blood samples are whole blood samples.

5. The method of claim 1, wherein in step (a) the macimorelin is administered in a composition comprising saccharin.

6. The method of claim 5, wherein the composition comprises 3.5% w/w macimorelin free base, 93.1% w/w spray-dried lactose monohydrate, 2.0% w/w Type A crospovidone, 0.1% w/w colloidal silicon dioxide, 1.0% w/w sodium stearyl fumarate, and 0.3% w/w saccharin sodium dihydrate.

7. A method for treating growth hormone deficiency in a child, comprising:

(1) selecting a child who has been determined as having growth hormone deficiency by the following process:
 (a) orally administering to the child about 1 mg per kg bodyweight of macimorelin;
 (b) measuring growth hormone level in
  (i) two blood samples taken from the child at about 30 minutes after step (a) and at about 45 minutes after step (a), or
  (ii) three blood samples taken from the child at about 30 minutes after step (a), at about 45 minutes after step (a), and at about 60 minutes after step (a),
  wherein no additional blood sample is taken from the child;
 (c) comparing highest growth hormone level in the blood samples obtained in step (b) with a predetermined threshold value of about 17 ng/ml; and
 (d) determining the child, whose highest growth hormone level in the blood samples obtained in step (b) is lower than the predetermined threshold value, as having growth hormone deficiency,
and
(2) injecting into the child an effective amount of a synthetic human growth hormone.

* * * * *